United States Patent

Narayanan et al.

Patent Number: 5,221,791
Date of Patent: Jun. 22, 1993

[54] WATER-SOLUBLE BIOLOGICALLY ACTIVE AMMONIUM SALTS

[75] Inventors: Kolazi S. Narayanan, Palisades Park; Ratan K. Chaudhuri, Butler; Robert B. Login, Oakland, all of N.J.

[73] Assignee: ISP Investments Inc., Wilmington, Del.

[21] Appl. No.: 705,200

[22] Filed: May 24, 1991

[51] Int. Cl.$^5$ ............................................. C07D 401/04
[52] U.S. Cl. .................................. 546/167; 536/28.54; 544/236; 544/311; 546/170
[58] Field of Search .................................. 546/167, 170

[56] References Cited

U.S. PATENT DOCUMENTS 4,931,566 6/1990 Suber et al. ........................ 546/167

Primary Examiner—C. Warren Ivy
Assistant Examiner—James H. Turnipseed
Attorney, Agent, or Firm—Jules E. Goldberg; Marilyn J. Maue; Joshua J. Ward

[57] ABSTRACT

This invention relates to hydrolysis resistant, water-soluble ammonium salt solids which are biologically active and which are described by the formula

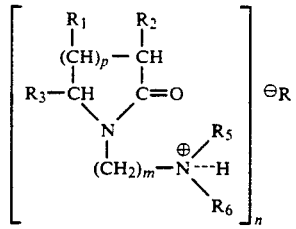

wherein m has a value of from 1 to 3; n has a value of from 1 to 4 and is equal to the free valences in anion R; p has a value of from 1 to 3; $R_1$, $R_2$ and $R_3$ are each independently selected from the group of hydrogen, and $C_1$ to $C_2$ alkyl; $R_5$ and $R_6$ are each independently selected from the group of hydrogen, hydroxyalkyl and alkoxyalkyl radicals having from 1 to 10 carbon atoms and R is the anion of a biologically active, water-insoluble anion having at least 1 deprotonized hydrogen and is derived from a biologically active, acidic, organic compound selected from the group of a carboxylic, thiocarbonic, sulfonic, sulfinic, thiosulfonic, thioacid, mono- and di- thiophosphate and phosphorous containing acid, having a pKa* value less than 5.

* negative logarithm, base 10. of the dissociation constant, Ka

3 Claims, No Drawings

WATER-SOLUBLE BIOLOGICALLY ACTIVE AMMONIUM SALTS

In one aspect the invention relates to stable, water soluble ammonium salts derived from water-insoluble, biologically active materials. In another aspect, the invention relates to the selective production of a stable, water-soluble pharmaceutical, herbicide, fungicide, insecticide, fumigant, or plant growth regulant in the form of a salt which has a significantly higher pH than its corresponding biologically active compound. Still another aspect of the invention pertains to compositions containing instant salt products and their use in specific fields of application dictated by the anionic moiety of said salt.

BACKGROUND OF THE INVENTION

Many organic carboxylic, phosphorous and/or sulfur-containing compounds are known to have superior biological properties which are beneficial in agricultural applications as insecticides, fungicides, fumigants and plant growth regulants; however, wide spread use of many of these products has been hampered by their water-insolubility. To overcome this problem, it has been necessary to form compositions involving the use of several components including surfactants, stabilizers and organic solvents, most of which are toxic or potentially toxic to animal, plant or marine life. Another solution to the problem is to form complexes of the water-insoluble chemicals with ammonia long chain amines or other solubilizing complexing agents. These methods have not resulted in a completely satisfactory solution since extraneous chemicals introduce some undesirable side effects and dilute the efficacy of the desired active component. It is particularly noted that the formulations containing surfactants cannot be used as aquatic herbicides or algicides since the surfactants have a deleterious affect on fish life. Complexes of the above water-insoluble biocides are also objectionable since they are easily hydrolyzed and must be applied shortly after complex formation. Hence, it has been the aim of research to provide such efficacious biologically active agents in a form which is resistant to hydrolysis for a more enduring effect and which is water-soluble to facilitate monitored dosage in aqueous sprays, most useful in agricultural applications.

Aqueous drug solutions have also attracted much interest in the field of local and systemic chemotherapy since such solutions introduce no extraneous or toxic chemicals and provide better drug penetration and a more immediate effect than tablet or capsule administration. However, no completely satisfactory solution has yet been developed, and the search continues for hydrolysis resistant, water soluble forms of normally water-insoluble pharmaceutical and agricultural chemicals which are easily manufactured and have good storage life.

Accordingly, it is an object of this invention to remedy the above deficiencies of biologically active water-insoluble compounds and to produce said compounds in a form which is resistant to hydrolysis and is substantially soluble in water.

Another object of this invention is to provide an economical, commercially feasible process for the preparation of said water soluble, hydrolysis resistant, biochemicals and drugs.

Still another object of the invention is to provide a product of high efficacy which is specific to plant life, fungus infection or insect attack and which does not require the use of a surfactant in its formulation.

These and other objects of the invention will become apparent to one skilled in the art from the following description and disclosure.

THE INVENTION

This invention relates to hydrolysis resistant, water-soluble ammonium salt solids which are biologically active and which are described by the formula

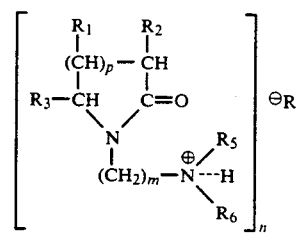

wherein m has a value of from 1 to 3; n has a value of from 1 to 4 and is equal to the free valences in anion R; p has a value of from 1 to 3; $R_1$, $R_2$ and $R_3$ are each independently selected from the group of hydrogen, and $C_1$ to $C_2$ alkyl; $R_5$ and $R_6$ are each independently selected from the group of hydrogen, hydroxyalkyl and alkoxyalkyl radicals having from 1 to 10 carbon atoms and R is the anion of a biologically active, water-insoluble organic compound having at least 1 deprotonized hydrogen and is derived from a biologically active, organic, acidic compound having from 2 to 24 carbon atoms which is selected from the group of a carboxylic, thiocarbonic, sulfonic, sulfinic, thiosulfonic, thioacid, arsanilic, mono- and di-thiophosphate and phosphorous containing acids and which has a pKa less than 5.

Of the above compounds, those having a pKa less than 4 and wherein $R_1$, $R_2$ and $R_3$ are hydrogen; n has a value of not more than 2 and R is a carboxylate, phosphate, phosphonate, thiophosphate, sulfonate, or arsanilate anion are preferred.

The water-soluble biologically active compounds referred to herein are those containing an acidic hydrogen which is capable of quaternizing the terminal nitrogen of the present lactam alkyl amine forming salt by protonization. These organic compounds having a protonizable hydrogen include carboxylic, thiocarbonic, sulfonic, sulfinic, thiosulfonic, thioloc and phosphorous containing acids shown on pages 528 through 534 of VAN NOSTRAND CHEMIST'S DICTIONARY, 1961. Representative examples of these biologically active compounds are listed in the following Table where the number of effectively dissociatable acidic hydrogen atoms are shown in parenthesis.

HERBICIDES

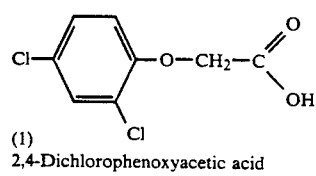

(1)
2,4-Dichlorophenoxyacetic acid

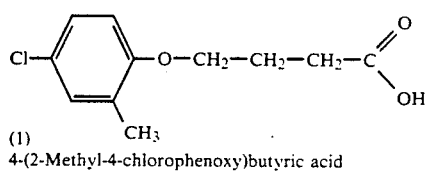
(1)
4-(2-Methyl-4-chlorophenoxy)butyric acid

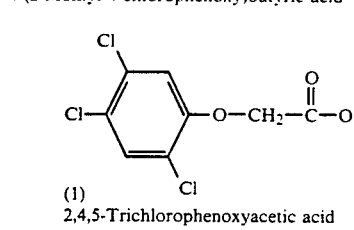
(1)
2,4,5-Trichlorophenoxyacetic acid

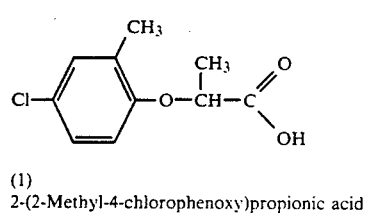
(1)
2-(2-Methyl-4-chlorophenoxy)propionic acid

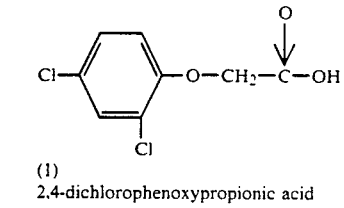
(1)
2,4-dichlorophenoxypropionic acid

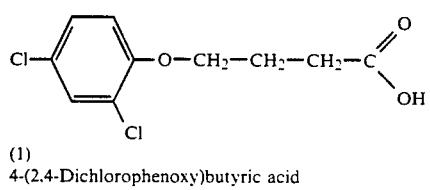
(1)
4-(2,4-Dichlorophenoxy)butyric acid

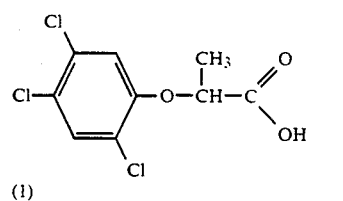
(1)
2-(2,4,5-Trichlorophenoxy)propionic acid

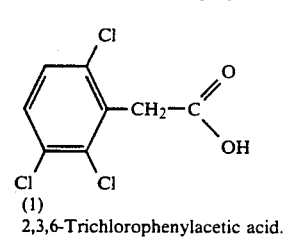
(1)
2,3,6-Trichlorophenylacetic acid.

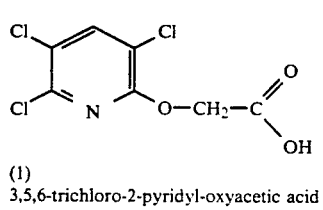
(1)
3,5,6-trichloro-2-pyridyl-oxyacetic acid

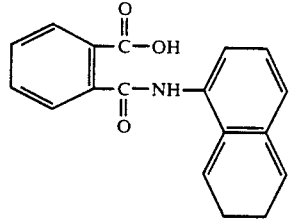
(1)
N-1-Naphthylphthalamic acid

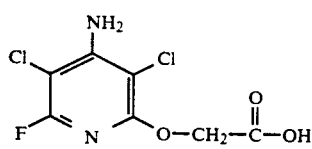
(1)
4-amino-3,5-dichloro-6-fluoro-2-pyridyloxyacetic acid

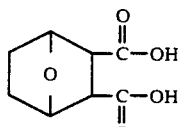
(1, 2)
7-oxabicyclo(2.2.1)heptane-2,3-dicarboxylic acid

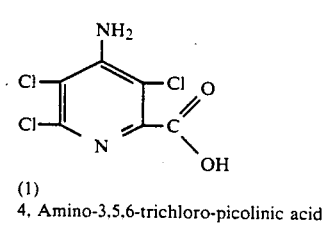
(1)
4, Amino-3,5,6-trichloro-picolinic acid

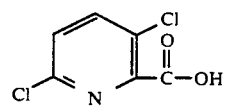
(1)
3,6-dichloro-2-pyridine carboxylic acid
3,6-Dichloropicolinic acid

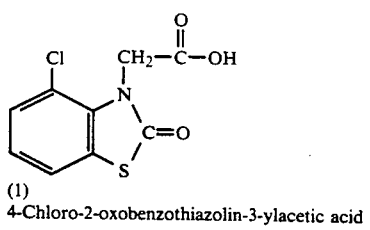
(1)
4-Chloro-2-oxobenzothiazolin-3-ylacetic acid

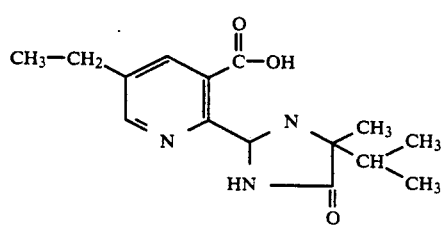
(1)
2-[4,5-dihydro-4-methyl-4-(1-methylethyl)-5-oxo-1 H imidazol-2-yl[-5-ethyl-3-pyridine carboxylic acid -continued

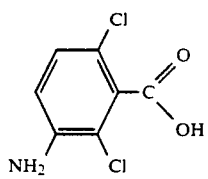
(1)
3-Amino-2,5-dichlorobenzoic acid.

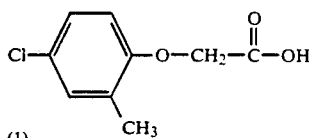
(1)
2-Methyl-4-chlorophenoxyacetic acid

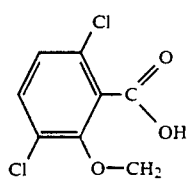
(1)
3,6-dichloro-O-anisic acid.

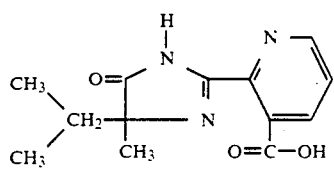
(1)
2-[4,5-dihydro-4-methyl-4-(1-methyl-ethyl)-5-oxo-1H-imidazol-2-yl]-3-pyridinecarboxylic acid

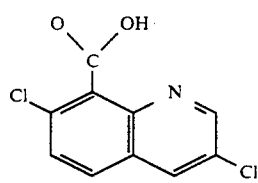
(1)
3,7-dichloro-8-quinoline carboxylic acid

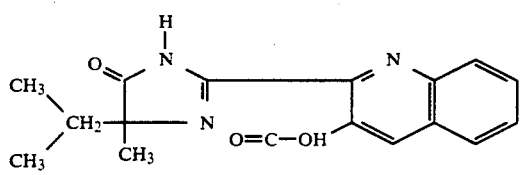
(1)
2-[4,5-dihydro-4-methyl-4-(1-methylethyl)-5-OXO-1 H-imidazol-2-yl]-3 quinoline carboxylic acid

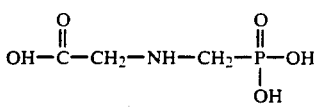
(1,2,3)
N-(phosphonomethyl)glycine

-continued

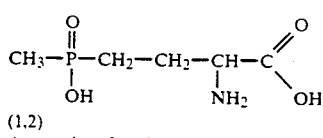
(1,2)
Ammonium(3-amino-3-carboxypropyl)-methylphosphinic acid

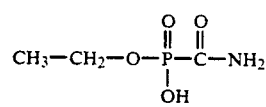
(1)
(aminocarbonyl)phosphonic acid

INSECTICIDES

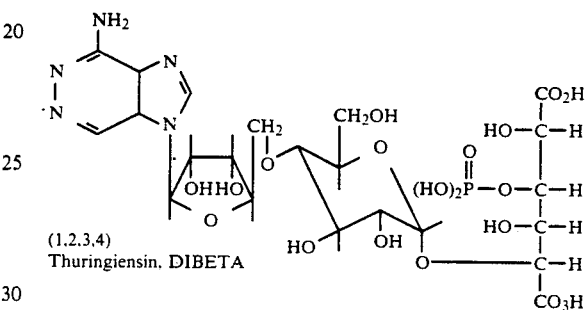
(1,2,3,4)
Thuringiensin, DIBETA

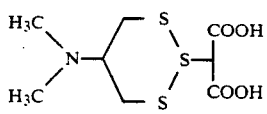
(1,2)
N,N-Dimethyl-1,2,3-trithian-5-ylamine hydrogenoxalate

FUNGICIDES
POLYOXIN

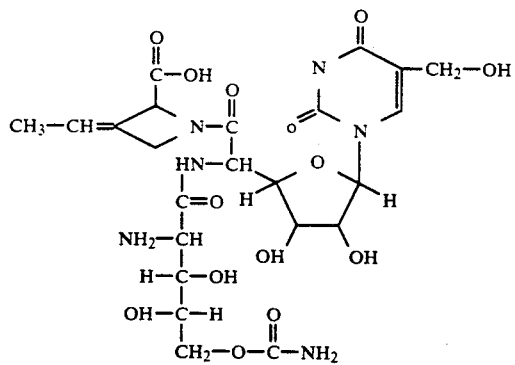
(1)
1-5-N-(5″-O-carbonyl-2″2 -deoxy-L-xylonyl-5′deoxy-beta-D-allofurano-syl-uronic acid)-5-hydroxymethyl uracid

FUMIGANTS, GROWTH REGULANTS, REPELLANTS AND RODENTICIDES

(1)
Butanedioic acid-(2,2-dimethylhydrazide)

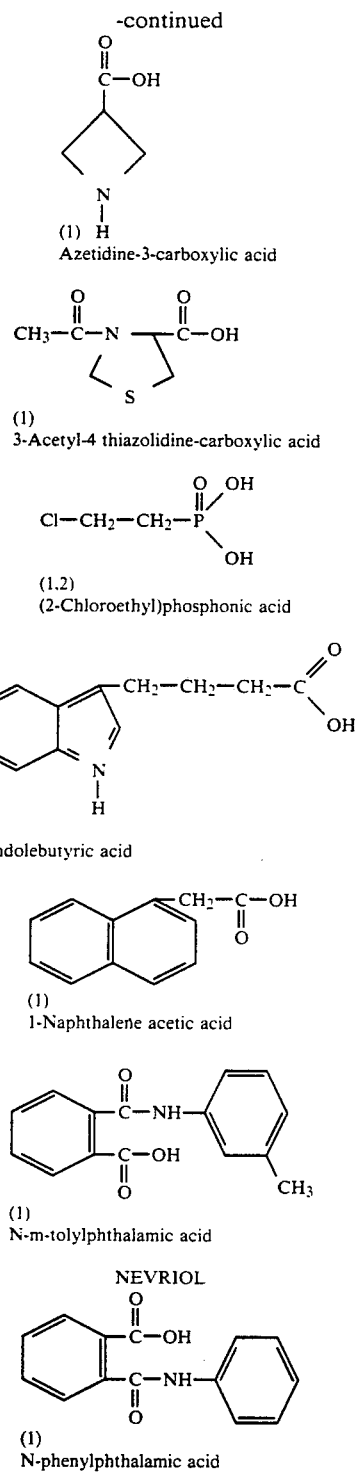

-continued

Azetidine-3-carboxylic acid (1)

3-Acetyl-4 thiazolidine-carboxylic acid (1)

(2-Chloroethyl)phosphonic acid (1,2)

3-Indolebutyric acid (1)

1-Naphthalene acetic acid (1)

N-m-tolylphthalamic acid (1)

NEVRIOL
N-phenylphthalamic acid (1)

Examples of water-insoluble pharmaceutical compounds having at least one acidic hydrogen include the following compounds wherein the number of dissociatable hydrogen atoms is shown in parenthesis.

| | |
|---|---|
| Ibuprofen (1), | Indoprofen (1), |
| Indobufen (1), | Indomethacin (1), |
| Clavulinic acids (1), | Aconiazide (1), |
| Acrivastine (1), | Acidic Aldesulfone (1,2), |
| Amineptine (1), | Acetyl salicylic acid (1), |
| Acetiromate (1), | Acexamic acid (10, |

-continued

| | |
|---|---|
| Acidic Aceflylline (1), | Acifran (1). |
| Acipimox (1), | Aminobenzoic acid (1). |
| Amoxicillin (1). | Benfotiamine. |
| Ceforamide (1,2). | Acidic Chiniofon (1). |
| Dinoprostone (1), | Acidic Docusate (1). |
| Etidronic acid (1,2,3,4), | Fosfosal (1,2,3). |
| Fosfocreatinine (1,2). | Carbarsone (1,2). |
| Isotretinoin (1). | Halazone (1). |
| Methyl dopa (1), | Meticillin (1), |
| Nalidixic acid (1), | Nedocromil (1,2), |
| Acidic Cyclamate (1), | Sulfoniazide (1), |
| Sulisatin (1,2) and | Phosphinic acid (1), |
| Thiobromineacetic acid (1), | Thenoic acid (1), |
| Sulisobenzene (1), | Sulindac (1), |
| Phthalic acid (1,2), | Phosphocreatine (1,2,3), and |
| Phytonadiol diphosphoric acid [Vitamin K-acid form (1,2,3,4)]. | |

The above pharmaceuticals include antibiotics, antidepressants, amebicides, antiseptics, disinfectants, laxatives, tonics, and antiiinflammatory, antihyperlipemic, antitubercular, antileprotic, antiasthamatic, dermological, antiprotozoal, analgesic, cardial, antiacne, antihypertensive and antiallergic agents.

The present products are characterized as having a hydrophilic moiety, represented by the quaternized pyrrolidonyl alkyl ammonium moiety which is electrostatically bonded to the anion and is thus significantly more soluble in water than the parent biologically active material The function of the product is specifically controlled by the selection of anion used to form the present ammonium salt. Of course, it is to be understood that mixtures of the present salts can be employed when one or more functions are desired.

The products of the present application are prepared by an economical and commercially feasible process which involves dissolving the water-insoluble component in a non-aqueous inert solvent such as for example, methanol, ethanol, isopropanol, acetone, methyl ethyl ketone, acetonitrile, toluene, methylene chloride, and the like or forming a suspension of the water-insoluble component in water and then contacting with the selected, non-quaternized lactam alkyl amine having the formula

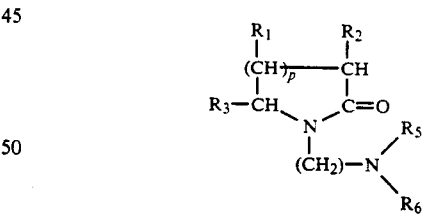

which is reacted at a temperature of between about 20° and about 90° C. under a pressure of from about atmospheric to about 50 psig. over a period of from about 10 minutes to about 2 hours. Preferred reaction parameters include a temperature of between about 30° C. and about 50° C. under atmospheric pressure for a period of from about 20 minutes to about 1 hour. When a non-aqueous solvent is employed, it is removed by evaporation or any other convenient method, for example by filtration in those cases where the resulting salt is insoluble in the organic solvent. Aqueous solutions of the products can be employed as such, or with additional dilution or concentration as needed, to perform their desired functions. Generally, the reaction solvent or dispersing agent employed in the synthesis reaction is present in a concentration of between about 10 wt. % and about 90 wt. %, preferably between about 30 wt. % and about 70 wt. %.

The mole ratio of the non-quaternized N-pyrrolidonyl alkyl amine to biologically active component ranges between about 1:1 and about 4:1, preferably between about 1:1 and about 2:1. Most preferably, the molar amount of reactant pyrrolidonyl alkyl amine is about equal to one or two of the hydrogen atoms in the biologically active or pharmaceutical compound. While sufficient pyrrolidonyl reactant can be used to quaternize all sites of dissociable and protonizable hydrogen atoms in compounds containing 4 or more acidic hydrogen atoms, reaction at more than two sites is usually not required to provide the desired water solubility in the product.

The products of the present invention can be used as aqueous dispersions, emulsions or solutions without further purification or they may be dried and used as granules, a fine powder or can be molded into tablets or the like. For agricultural applications, the present products are beneficially applied as aqueous solutions, emulsions or dispersions wherein the concentration of the active product is between about 0.1 and about 95%; more often between about 0.75 and about 50%. Formulations of the present products can include a surfactant, if desired, together with other adjuvants such as wetting agents, diluents, rheology modifiers, buffering agents, binders and disintegrating agents. Pharmaceutical formulations generally include between about 0.01 and about 900 mg, preferably between about 1 and about 500 mg concentration of the present products which can be administered as a tablet, capsule, powder, lotion, paste, or solution or in a formulation which may include other medicinal components. Such formulations may be prepared by simply mixing the desired components at ambient temperature and pressure.

Having thus described the invention, reference is now had to the following examples which illustrate preferred embodiments but which are not to be construed as limiting to the scope of the invention as more broadly set forth above and in the appended claims.

EXAMPLE 1

A 500 ml round bottomed flask was charged with 150g of methanol to which was added 30 g commercially available (Dicamba) 3,6-dichloro-1-methoxy benzoic acid which was 90% pure. The mixture was stirred at room temperature until the complete dissolution occured. To the solution was added 15.8 g of 98.5% pure amino ethyl pyrrolidone (AEP) over a period of 30 minutes during which a slight exotherm occurred. The mixture was then stirred for about 30 minutes, after which the solvent was removed by rotary evaporation leaving a slightly oily product. The product was purified by titurating with acetone (200-300 ml) until a white crystalline solid (m.p.=18°-20° C.) was produced weighing 28 g, representing a 65% yield of 99.5% pure N-pyrrolidonyl ethyl ammonium salt of 3,6-dichloro-1-methoxy benzoic acid.

The purity of the product was determined by potentiometric titration of a methanolic solution of the salt by alkali (NaOH) and acid (HCl). The composition of the product was established by elemental analysis, reported as follows:

|   | Calculated | Found |
|---|---|---|
| % C | 48.14 | 47.73 |
| H | 5.16 | 5.25 |
| N | 8.02 | 7.87 |
| Cl | 20.34 | 20.42 |

IR (Infra red) spectra and $^1H$ and $^{13}C$ NMR spectra were consistent with the structure assigned.

A stable solution of the above ammonium salt was easily dissolved in 60% water; whereas the 3,6-dichloro-1-methoxy benzoic acid had very poor solubility (<0.1%) in water.

EXAMPLE 2

Example 1 was repeated, except that 2 g of heavy water replaced 150 g of methanol solvent, 0.3 g of Dicamba replaced 30 g Dicamba and 0.16 g of AEP replaced 15.8 g of AEP. The resulting ammonium salt of Dicamba had the same NMR spectral analysis as in Example 1 showing that the salt exists in solution even without isolation.

The above experiments show that the AEP salt can be easily solubilized in water and can be prepared as a concentrated solution, which can be diluted to a desired concentration prior to application.

EXAMPLE 3

In a 250 ml round bottom flask 15.5 g (0.482 millimole) of a commercial herbicide, imazaquin* (97.4% pure, having an average molecular weight of 311.4) was suspended in 100 g water. To the suspension, 6.1 g (0.469 millimole) of 98.5% pure AEP was added. The mixture was stirred for 1 hour and produced a clear solution within 15 minutes. The solution was then filtered through Whatman paper #4 and the pH of the filtrate was found to be 7.2. The filtrate was then freeze dried to produce 18.0 g of the hygroscopic solid ammonium salt of imazaquin. The freeze-dried solid (0.1 g), dissolved completely in 50 g of water, which established the solubility of the ammonium salt product.

* 2-[4,5-dihydro-4-methyl-4-(methylethyl)-5-oxo-1H-imidazol-2-yl]-3-quinoline e carboxylic acid.

The freeze-dried solid, was analyzed for its spectral properties via IR and $^1H$ NMR spectral data. The spectral data indicate the structure of the N-pyrrolidonyl ethyl ammonium salt of imazaquin.

EXAMPLE 4

A solution containing 25 g of the AEP salt of commercial imazaquin in water was prepared from a suspension of 25 g of imazaquin in 50 g water to which was added a stoichiometric amount of AEP (10.2 g) and an additional 15 g of water. The solution was stirred for 30 minutes after which it was filtered and the pH of the filtrate was adjusted to 7.2.

The resulting solution was found to be stable under ambient conditions without any precipitation when stored for 6 months. Also, after cooling to 0° C. and then allowing to heat to room temperature, no precipitation was observed.

The above experiment shows that 35% of the present ammonium salt of water insoluble imazaquin derived from 25% of the imazaquin can be solubilized in water as a stable AEP salt product and can be manufactured as a useful, water-soluble concentrate.

EXAMPLE 5

To a solution containing 13 g (0.1 mole) AEP (98.5% pure) dissolved in 30 g water in a 100 ml round bottom flask was added at 25° C. and with constant agitation, 16.9 g (0.1 mole) of water insoluble solid phosphonomethyl glycine. The solid phosphonomethyl glycine reacted to form the corresponding AEP salt and completely dissolved in the water within 30 minutes, during which an exotherm to 35°–40° C. was noted. The water was removed by rotary evaporation, which produced an oily liquid from which the pure salt product was isolated by tituration with methanol and then with acetone followed by filtration and drying to produce the AEP salt of phosphonomethyl glycine which is more than 50% soluble in water.

$^1$H and $^{13}$CNMR data indicated the structure of the product to be the N-pyrrolidonyl ethyl ammonium salt of phosphonomethyl glycerine. Thus, the water soluble salt of phosphonomethyl glycine can be produced and stored as a stable aqueous concentrate for subsequent use.

EXAMPLE 6

The commercial product "Spot Weeder", from Johnson Wax contains an aqueous solution of a wetting agent and an active mixture of herbicidal dimethyl amine salts of (a) 2,4-dichlorophenoxy acetic acid* (0.583%), (b) 2-(4-chloro-2-methylphenoxy) propanoic acid** (0.287%) and (c) 3,6-dichloro-2-methoxy benzoic acid (0.066%).
* 2,4-D
** Mecoprop For the purposes of experimentation, a water soluble composition was made containing the same mole percent of (a), (b) and (c) and formulated as the corresponding AEP salts, by the addition of stoichiometric amounts of AEP to (a), (b) and (c) according to the following procedure.

To one liter of water was added 15.42 g of 2,4D+7.11 g of mecoprop+1.83 g of 90% pure dicamba. After which 13.83 g AEP was added to the mixture. The resulting solution was stirred for 30 minutes to produce a completely water soluble product of active ingredients in the form of AEP salts. To the above solution was added 9 g of polyalkylene oxide modified by polydimethyl siloxane (Silvelt 7607 wetting agent) from Union Carbide. The mixture was stirred and the total weight was adjusted to 3000 g by adding water.

This solution was compared with commercial "Spot Weeder" by spraying on side by side 10'×10' plots. The present salt showed distinct advantages over "Spot Weeder" in that the rate of weed kill was significantly higher.

EXAMPLE 7

A suspension of 169 g of phosphonomethyl glycine in 301 g water was prepared and 130 g 98.5% pure AEP was added slowly with stirring until all of the phosphonomethyl glycine dissolved as the AEP salt. The resulting solution, (containing 28% of the active ingredient expressed as the free acid or 49.5% of the active ingredient expressed as the AEP salt) was evaluated as an aquatic herbicide and as a broad spectrum growth inhibitor for broad leaf plants and perennial weeds and compared with the isopropyl amine salt of phosphonomethyl glycine.

Results showed significantly higher and more permanent kill for the present AEP salt.

Following the procedure of the above examples, other lactam alkyl amines can be substituted for AEP to produce the corresponding water soluble salts of the indicated water insoluble biologically active compounds. Particularly recommended as lactam amines are the aminopropyl pyrrolidones, aminobutyl pyrrolidones, N,N'-di(hydroxyethyl) ethyl amino pyrrolidone, aminomethyl caprolactams and aminoethyl valerolactams. Similarily, other biologically active water insoluble compounds or drugs having one or more acidic hydrogen atoms can be substituted in the above examples, or with other lactam amines indicated herein, to provide desirable water soluble salts.

What is claimed is:

1. A biologically active compound having the formula

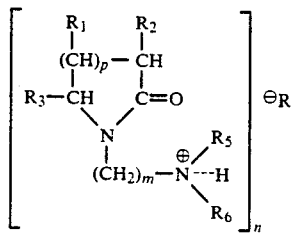

wherein m has a value from 1 to 3; n has a value of from 1 to 4 and is equal to the free valences in anion R; p has a value of from 1 to 2; $R_1$, $R_2$ and $R_3$ are each independently selected from the group of hydrogen, and $C_1$ to $C_2$ alkyl; $R_5$ and $R_6$ are each independently selected from the group of hydrogen, hydroxyalkyl and alkoxyalkyl radicals having from 1 to 10 carbon atoms and R is the anion of a biologically active, water-insoluble organic compound having at least 1 deprotonized hydrogen and derived from a biologically active carboxylic acid substituted quinoline group having a pKa value less than 5.

2. The compound of claim 1, selected from the group consisting of 3,7-dichloro-8-quinoline carboxylic acid and 2-[4,5-dihydro-4-methyl-4-(1-methylethyl)-S-OXO-1 H-imidazol-2-yl]-3 quinoline carboxylic acid.

3. The compound of claim 1 wherein R is an anion of imazaquin.

* * * * *